United States Patent [19]
Ramirez de Agudelo et al.

[11] Patent Number: 5,948,942
[45] Date of Patent: *Sep. 7, 1999

[54] BIMETALLIC CATALYST FOR THE SIMULTANEOUS SELECTIVE HYDROGENATION OF DIOLEFINS AND NITRILES AND METHOD OF MAKING SAME

[75] Inventors: Magdalena Ramirez de Agudelo, Miranda; Djamal Djauadi, La Morita Res. Sierra; Julia Guerra, San Antonio, all of Venezuela

[73] Assignee: Intevep, S.A., Caracas, Venezuela

[*] Notice: This patent is subject to a terminal disclaimer.

[21] Appl. No.: 08/934,243

[22] Filed: Sep. 19, 1997

Related U.S. Application Data

[63] Continuation-in-part of application No. 08/902,183, Jul. 29, 1997, abandoned, which is a continuation of application No. 08/585,950, Jan. 16, 1996, Pat. No. 5,663,446, which is a division of application No. 08/354,969, Dec. 13, 1994, Pat. No. 5,523,271.

[51] Int. Cl.⁶ .......................... C07C 209/00; C07C 17/20; B01J 21/00
[52] U.S. Cl. ............................. 564/490; 502/74; 570/260
[58] Field of Search .............................. 564/490; 502/74; 570/260

[56] References Cited

U.S. PATENT DOCUMENTS

| | | |
|---|---|---|
| 4,152,351 | 5/1979 | Drake . |
| 4,271,323 | 6/1981 | Durand et al. . |
| 4,734,540 | 3/1988 | Gattuso et al. . |

*Primary Examiner*—Paul J. Killos
*Attorney, Agent, or Firm*—Bachman & LaPointe, P.C.

[57] ABSTRACT

A catalyst useful for the simultaneous and selective hydrogenation of diolefins and nitriles present in a hydrocarbon feedstock includes (a) a support material selected from the group consisting of inorganic oxide, carbon, zeolite and mixtures thereof; and (b) a catalytically active metal phase including at least two metals selected from the group consisting of at least partially reduced Group IB metals and completely reduced Group VIII metals, the active metal phase being present in an amount of about $\geq 0.03$ wt %.

26 Claims, No Drawings

BIMETALLIC CATALYST FOR THE SIMULTANEOUS SELECTIVE HYDROGENATION OF DIOLEFINS AND NITRILES AND METHOD OF MAKING SAME

CROSS REFERENCE TO RELATED APPLICATIONS

This application is a continuation-in-part of U.S. patent application Ser. No. 08/902,183, filed Jul. 29, 1997, now abandoned which is a continuation of U.S. patent application Ser. No. 08/585,950, filed Jan. 16, 1996, now U.S. Pat. No. 5,663,446 which is a divisional of U.S. patent application Ser. No. 08/354,969, filed Dec. 13, 1994, now U.S. Pat. No. 5,523,271.

BACKGROUND OF THE INVENTION

The present invention relates to a bimetallic catalyst material for use in the hydrogenation of hydrocarbon feedstocks and, more particularly, to a catalyst which is useful for the simultaneous and selective hydrogenation of diolefins and nitriles present in a hydrocarbon feedstock.

There are known in the prior art processes and catalysts for hydrogenating unsaturated compounds in liquid hydrocarbon feedstocks. For example, U.S. Pat. No. 4,152,351 discloses a process for the hydrogenation of an olefinic unsaturation. More specifically, it relates to the catalytic hydrogenation of aliphatic, unsaturated compound in the presence of a palladium hydrogenation catalyst on a suitable support. Still more specifically, the invention relates to the use of applicable additives for a palladium hydrogenation catalyst used to hydrogenate the olefinic unsaturation. Further, the invention relates to the hydrogenation of aliphatic, unsaturated compounds containing nitrile groups. U.S. Pat. No. 4,271,323 discloses a process for hydrogenating unsaturated compounds in the liquid phase in the presence of a soluble catalyst obtained by reacting an organometal derivative or a metal hydride with a synergistic mixture of (a) a compound of zinc, zirconium, manganese, molybdenum, or iron and (b) a nickel or cobalt compound. U.S. Pat. No. 4,734,540 discloses a process which is useful for the selective hydrogenation of polyunsaturated organic compounds. The resultant product of such a reaction produces the monoolefinic equivalents of the hydrogenated polyunsaturated organic compounds. The catalyst used in this selective hydrogenation process comprises nickel and sulfur deposited on the surface of an alumina support. The preferred catalyst does not contain halogens, noble metals, alkaline earth metals, or alkali metals and is characterized by having only a very low percentage of the total pore volume being provided by pores having an average pore diameter less than 150 angstroms. The great majority of the pore volume is present in the form of macropores having diameters of 500 to 1500 angstroms.

While the foregoing processes employ catalysts which are useful in the hydrogenation process, the processes and catalysts are not as selective nor do they simultaneously hydrogenate diolefins and nitriles. Naturally, it would be highly desirable to provide a catalyst which is useful for the simultaneous selective hydrogenation of diolefins and nitriles in a hydrocarbon feedstock.

Accordingly, it is the principle object of the present invention to provide a catalyst useful for the simultaneous and selective hydrogenation of diolefins and nitriles present in a hydrocarbon feedstock.

It is a further object of the present invention to provide a method for preparing a catalyst as aforesaid.

It is a still further object of the present invention to provide a process for the simultaneous and selective hydrogenation of diolefins and nitriles from a hydrocarbon feedstock employing such a catalyst.

It is another object of the present invention to provide a bimetallic catalyst for the simultaneous selective hydrogenation of diolefins and nitriles, a method for making such a bimetallic catalyst, and a process using such a catalyst.

Further objects and advantages of the present invention will appear hereinbelow.

SUMMARY OF THE INVENTION

The present invention relates to a catalyst useful for the simultaneous and selective hydrogenation of diolefins and nitriles present in a hydrocarbon feedstock. The support material is preferably selected from the group consisting of an inorganic oxide-zeolite composite, carbon and zeolite. A catalytically active phase is deposited on the support material. The catalytically active metal phase is selected from the group consisting of partially reduced Group IB metals and completely reduced Group VIII metals. The catalytically active metal phase is present in an amount of $\geq 0.03$ wt %.

In accordance with a preferred embodiment of the present invention, the catalytically active phase preferably comprises at least two active metals selected from the group consisting of partially reduced Group IB metals and completely reduced Group VIII metals.

The catalyst of the present invention is particularly useful in a process for the simultaneous and selective hydrogenation of diolefins and nitriles present in a hydrocarbon feedstock. The catalyst of the present invention is prepared by impregnating the support material with a solution of the active metal phase, drying the impregnated support and calcining. The dried and calcined support is thereafter activated to the proper reduction state. The catalyst is used in a hydrogenation process wherein the hydrocarbon feedstock in the presence of the catalyst and hydrogen is treated at a temperature of between about 50 to 250° C. and a pressure of 150 to 650 psi so as to selectively hydrogenate diolefins and nitrites from the hydrocarbon feedstock.

The bimetallic catalyst of the present invention is preferably prepared by impregnating the support material with a single solution containing all desired Group VIII metals, and/or by incorporating Group IB metals by successive impregnation with intermediate calcination and activation after each impregnation step.

DETAILED DESCRIPTION

The catalyst of the present invention is particularly useful in a process for the simultaneous selective hydrogenation of diolefins and nitrites.

The catalyst of the present invention comprises a support material having a catalytically active metal phase deposited thereon. Suitable support materials include inorganic oxide-zeolite composites, carbon and zeolite. Preferably, the support material is selected from the group consisting of inorganic oxides, carbon, zeolite and mixtures thereof. Suitable inorganic oxides are selected from the group consisting of silica, alumina, clay, titania, magnesia, and mixtures thereof, as well as other molecular sieve materials and the like. Particularly suitable support materials include zeolite-clay and alumina-zeolite.

The support material has deposited thereon a catalytically active metal phase selected from the group consisting of Group IB metals and Group VIII metals of the Periodic Table. Depending on the active metal employed, the amount of the metal active phase present on the catalyst may vary. The active metal should be present in a minimum amount of about ≧0.03 wt % up to 25 wt %. Particularly suitable active metal materials include copper, nickel, iron, cobalt and palladium.

Preferably, the metal active phase includes at least two metals selected from the group consisting of completely reduced Group VIII metals and partially reduced Group IB metals. Particularly suitable combinations of active metals include nickel/copper, nickel/cobalt, and nickel/iron. In accordance with the present invention, it has been found that the bimetallic catalyst in accordance with the present invention, having at least two different metals selected from Group VIII and Group IB metals, provides excellent performance in processes for selective and simultaneous hydrogenation of diolefins and nitriles.

As noted above, particularly suitable support material for use in the catalyst of the present invention is an alumina-zeolite composite. It has been found that the surface area of the resulting catalyst should be between about 100 to 1500 $m^2/g$, preferably between 100 to 1000 $m^2/g$ and ideally between about 250 to 350 $m^2/g$. The pore volume of the catalyst is preferably between 0.20 cc/g to 1.50 cc/g, preferably 0.30 cc/g to 0.70 cc/g.

In order for the catalyst of the present invention to be effective in the simultaneous selective hydrogenation of diolefins and nitriles, it has been found that the metal active phase must be reduced to the right state in order to be effective. In accordance with the present invention the Group IB metals must be partially reduced while the Group VIII metals must be completely reduced. By partial reduction it is meant that metal sites consist of one or more than one oxidation state different than zero, more particularly catalyst exhibit metal sites with a net charge on them. By complete reduction it is meant the metal sites largely consist of a single species, more particularly the highest number of species exhibit the elemental state of charge, i.e., zero.

In accordance with the preferred embodiment of the present invention wherein at least two metals are provided, calcination and activation are carefully controlled so as to provide partially reduced Group IB metals, and completely reduced Group VIII metals as desired.

The catalyst of the present invention is prepared by impregnating the support material with a solution containing the catalytically active metal phase for example in the form of metal salts. As noted above the metal active phase should be present in an amount on the final catalyst of about ≧0.03 wt %. The impregnated support material is thereafter dried and calcined at a temperature of between 150 and 600° C. for a time sufficient to decompose the metal salt impregnated on the catalyst support. Particularly suitable metal salts used in the aqueous solution for impregnating the catalyst material include $Cu(NO_3)_2*2.5\ H_2O$; $(NiNO_3)_2*6H_2O$; and $(CH_3COO)_2Pd$, although other solutions may be used. The dried and calcined catalyst is thereafter activated to the proper reduction state depending on the type of active metal phase employed. Partial reduction of the Group IB metals are accomplished under the following conditions: Temperature (°C.) 150–300, Pressure (psi) 15–350, $H_2$ flow rate (lt/h) 0.1–8.0. Complete reduction of the Group VIII is achieved under the following conditions: Temperature (°C.) 200–600, Pressure (psi) 15–350, $H_2$ flow rate (lt/h) 0.1–8.0. Generally, it is preferred that temperature be less than about 350° C. and pressure be less than about 250 psi for partial reduction, and that temperature be greater than about 400° C. and pressure be greater than about 250 psi for total reduction.

In connection with the preparation of bimetallic catalyst in accordance with the present invention, when two or more Group VIII metals are to be impregnated on the support, it is preferred that these metals be deposited on the support material by impregnation with a single solution containing each of the desired Group VIII metals. If the active metal phase of the bimetallic catalyst in accordance with the present invention is to contain one or more Group IB metals, it is preferred that the Group IB metal be incorporated or impregnated on the support material separately, preferably after the Group VIII metals, by successive impregnation using a solution of the Group IB metal. If more than one Group IB metal is to be used, each metal may be impregnated using a separate solution. Each successive impregnation is preferably followed by intermediate calcination and activation to the desired state of reduction.

In general, it is preferred that the support be impregnated first with a solution containing any Group VIII metal(s) to be used, followed by calcination and activation to at least partially reduce the Group VIII metal(s), and any desired Group IB metal is then impregnated onto the Group VIII metal impregnated catalyst, again followed by calcination and activation so as to partially reduce the Group IB metal as desired, and complete reduction of the Group VIII metal (s).

It has also been found, however, that when using zeolite-alumina as a support, the support may be impregnated first with the Group IB metal, and calcined and activated to partial reduction of the Group IB metal, followed by impregnation with Group VIII metal(s), and calcination and activation to completely reduce the Group VIII metal(s). In this instance, it has been found that the alumina of the support stabilizes the partially reduced Group IB metal species so that the Group IB metal remains partially reduced through the complete reduction of the Group VIII metal(s).

Other impregnation sequences may also be used, including for example co-impregnation, but the above described successive impregnations are preferred.

For the preferred bimetallic catalyst of the present invention, metals are preferably provided having a metal atomic ratio in the range of between 1:100 to about 100:1, depending upon the metals to be used, and the total metal content is preferably between about 0.03 wt % to about 25 wt % based upon the total weight of the final catalyst.

Also, as set forth above, metals of the bimetallic catalyst in accordance with the present invention may suitably be partially reduced by treating the catalyst at a temperature less than or equal to about 350° C., at a pressure of less than or equal to about 250 psi and for a time of less than about 15 hours, while catalyst may suitably be reduced totally or completely through treatment at temperatures above 400° C., at hydrogen pressures of greater than about 250 psi, and for time periods of at least about 8 hours.

The catalyst of the present invention prepared in accordance with the method described above is particularly useful in processes for the simultaneous and selective hydrogenation of diolefins and nitriles from a hydrocarbon feedstock. The hydrocarbon feedstock in the presence of the catalyst is mixed with hydrogen wherein the ratio of the hydrogen to the diolefins and nitriles in the feedstock is less than three times the stoichiometric amount required to selectively hydrogenate diolefins and nitriles. The hydrogen, hydrocarbon feedstock and catalyst are treated in a reactor at a temperature of between 50 to 250° C. at a pressure of between 150 to 650 psi. The preferred conditions for the hydrogenation process are a temperature of between 70 to 160° C. at a pressure of between 200 to 400 psi at a liquid hourly space velocity of between 0.1 to 5 h$^{-1}$, preferably 0.5 to 5 h$^{-1}$, ideally 1 to 4.5 h−1.

The advantageous features of the catalyst of the present invention and method for preparing same will become clear from the following examples.

EXAMPLE 1

This example demonstrates the process for making the catalyst of the present invention employing an inorganic oxide-zeolite composite support having a Group VIII activated metal phase deposited thereon.

An alumina-zeolite composite support of the type disclosed in U.S. Pat. No. 4,762,537 and sold by Alcoa Aluminum Corporation under the trademark Selexsorb was selected as the catalyst support material. Four of the catalysts supports were impregnated with solutions of nickel nitrate of different concentrations. A fifth catalyst was prepared by impregnating the catalyst support with palladium. The five impregnated catalysts were dried and calcined so as to decompose the salts of the incorporated active metal. The calcined impregnated catalysts supports were then activated under controlled temperature and time conditions so as to completely reduce or partially reduce the active metal phase. For complete reduction, the catalysts were treated at a temperature of 450° C. at 250 psi for 8 hours. Partial reduction was carried out at 250° C. for 8 hours at 200 psi. Table 1 below sets forth the catalyst composition and activation treatment for each of the five catalysts.

TABLE 1

| Catalyst | Support | Active Metal Phase | Activation |
|---|---|---|---|
| 1 | alumina-zeolite | 0.93 wt % Ni | completely reduced |
| 2 | alumina-zeolite | 5.7 wt % Ni | completely reduced |
| 3 | alumina-zeolite | 5.7 wt % Ni | partially reduced |
| 4 | alumina-zeolite | 12.90 wt % Ni | completely reduced |
| 5 | alumina-zeolite | 0.30 wt % Pd | completely reduced |

EXAMPLE 2

This example demonstrates the catalyst activity for the catalysts of Example 1 for the simultaneous and selective hydrogenation of diolefins and nitriles present in hydrocarbon feedstocks.

The activity for the simultaneous selective hydrogenation was determined during a 4 hour run using a synthetic C5 hydrocarbon feedstock having the composition set forth below in Table 2.

TABLE 2

| Synthetic Feedstock Composition | |
|---|---|
| C5 | 97.5% |
| Propionitrile | 0.5% |
| Diolefins | 0.5% |
| Monoolefins | 1.0% |

Eight cc's of each of the activated catalysts set forth in Example 1 were employed in a reactor for treating the hydrocarbon feedstock of Table 2. The reaction took place for 3 hours at a temperature of 120° C. and a pressure of 250 psi. The ratio by volume of hydrogen fed to the reactor with respect to the diolefins and nitriles was maintained at 3. The liquid space velocity (LHSV) of hydrogen feed was set at 3h−1. The results for each run employing the catalysts of Example 1 are set forth herein below in Table 3.

TABLE 3

| Catalyst | % Conversion Diolefins | % Conversion Monoolefins | % Conversion Nitriles |
|---|---|---|---|
| 1 | 100 | 59 | 86 |
| 2 | 100 | 78 | 100 |
| 3 | 0 | 0 | 0 |
| 4 | 100 | 0 | 100 |
| 5 | 100 | 0 | 88 |

As can be seen from Table 3 the concentration of the active metal phase of the Group VIII metal employed have an effect on the selective hydrogenation of the diolefins and nitriles in the hydrocarbon. Nickel concentrations of below 6 wt % were insufficient to insure selective hydrogenation. Catalyst 1 having a nickel concentration of 0.93 wt % was in fact not selective. At the same time, as can be seen from the results employing catalyst 5, 0.3 wt % palladium is sufficient for insuring selective hydrogenation of diolefins and nitrites. In addition, when comparing the results obtained from hydrogenation of feedstocks with catalysts 4 and 3, it can be seen that the Group VIII metals must be completely reduced in order for the catalyst to be active for the hydrogenation of diolefins and nitriles. specifically, catalyst 3 which contained 5.7 wt % nickel partially reduced did not achieve any conversion of either olefins, monoolefins or nitriles.

EXAMPLE 3

This example demonstrates the process for making the catalyst of the present invention employing an inorganic oxide-zeolite composite support having a Group IB active metal phase deposited thereon.

Three alumina-zeolite composite supports were impregnated with solutions of copper nitrate of different concentrations. The three impregnated catalysts were dried and calcined so as to decompose the salts of the incorporated active metal. Two of the calcined impregnated catalyst supports were activated by carrying out partial reduction of the active metal phase at 250° C. for three hours. The third impregnated catalyst support was completely reduced under the same conditions set forth in Example 1. Table 4 below sets forth the catalyst composition and activation treatment for each of the three catalysts.

TABLE 4

| Catalyst | Support | Active Metal Phase | Activation |
|---|---|---|---|
| 6 | alumina-zeolite | 0.79 wt % Cu | partially reduced |
| 7 | alumina-zeolite | 5.9 wt % Cu | partially reduced |
| 8 | alumina-zeolite | 5.8 wt % Cu | completely reduced |

EXAMPLE 4

This example demonstrates the catalyst activity for the catalysts of Example 3 for the simultaneous and selective hydrogenation of diolefins and nitrites present in hydrocarbon feedstocks.

The synthetic feedstock set forth Table 2 of Example 2 was processed employing the catalysts of Example 3 under the same conditions described above in Example 2. The results of each run employing the catalysts of Example 3 are set forth hereinbelow in Table 5.

TABLE 5

| Catalyst | % Conversion Diolefins | % Conversion Monoolefins | % Conversion Nitriles |
|---|---|---|---|
| 6 | 98 | 0 | 21 |
| 7 | 99 | 0 | 82 |
| 8 | 0 | 0 | 0 |

As can be seen from Table 5, as was the case with the Group VIII metals discussed above, the concentrations of the active metal phase of the Group IB metals employed have an affect on the selective hydrogenation of the diolefins and nitriles in the hydrocarbon. Copper concentrations as low as 0.80 wt % were effective for the selective and simultaneous hydrogenation of diolefins and nitriles. In addition to the foregoing, the degree of reduction of the metal phase affects the activity of the Group IB metal. However, contrary to the Group VIII metals, the Group IB metals are effective when partially reduced and ineffective when completely reduced. In this regard see Catalyst No. 8 wherein the copper metal phase was completely reduced and no conversation of diolefins, monoolefins or nitriles was accomplished.

EXAMPLE 5

This example demonstrates the importance of the catalyst support on the activity of the catalyst of the present invention.

Carbon granules provided by Johnson Matthey were selected as one catalyst support. A second catalyst support comprising gamma alumina sold by Johnson Matthey under was likewise selected. Both of the supports were impregnated with palladium in the manner described above with regard to Example 1 and the impregnated catalyst supports were then activated by complete reduction at a temperature of 450° C., a pressure of 250 psi for eight hours. Table 6 below sets forth the catalyst composition and activation treatment for each of the two catalysts.

TABLE 6

| Catalyst | Support | Active Metal Phase | Activation |
|---|---|---|---|
| 9 | gamma alumina | 1.0 wt % Pd | completely reduced |
| 10 | carbon | 0.3 wt % Pd | completely reduced |
| 11 | gamma alumina | 0.3 wt % Pd | completely reduced |

EXAMPLE 6

In order to demonstrate the catalyst activity for the catalysts of Example 5 for the simultaneous and selective hydrogenation of diolefins and nitriles, the synthetic feedstock of Example 2 was treated with the catalysts under the same conditions set forth in Example 2. The results for each run employing the catalysts of Example 5 are set forth below in Table 7.

TABLE 7

| Catalyst | % Conversion Diolefins | % Conversion Monoolefins | % Conversion Nitriles |
|---|---|---|---|
| 9 | 100 | 88 | 18 |
| 10 | 100 | 0 | 50 |
| 11 | 100 | 30 | 20 |

The carbon supported catalyst, catalyst 10, was effective for the simultaneous hydrogenation of diolefins and nitriles in a selective manner wherein the gamma alumina supported catalysts (9 and 11) achieved no selective conversion of diolefins, monoolefins or nitriles. The results lead one to conclude that carbon and the zeolite present in the inorganic oxide-zeolite composite are effective catalyst supports for the catalysts of the present invention. Both the zeolite and carbon contain moderate Lewis acid sites which are believed to be responsible for the superior activity characteristics of the catalysts of the present invention.

EXAMPLE 7

This example illustrates the method of preparation of bimetallic catalyst in accordance with the present invention, using a mixture of zeolite and alumina or zeolite and clay as support for metal phases including only nickel, nickel/copper, nickel/cobalt and nickel/iron. The support is previously calcined. Group VIII metal(s) is/are deposited by impregnation from a single solution. Group IB metal was then successively impregnated onto the support using a solution of the Group IB metal, with intermediate calcination or activation after each impregnation under conditions to partially reduce the Group IB metal and completely reduce the Group VIII metal(s). Each catalyst contains 8% wt. total metal.

The impregnated catalysts are activated by carefully controlling time and temperature in order to achieve total or partial reduction as desired. For a total reduction, the catalysts were treated at temperatures above 400° C., hydrogen pressures above 250 psi and for a time longer than 8 hours. For partial reduction the catalysts were treated at temperatures below 350° C., pressure below 250 psi and for a time shorter than 15 hours. The catalysts prepared as set forth above are further described in Table 8 below.

This example also illustrates catalytic performance of catalysts prepared as above, using a C5 naphtha feedstock containing 2 wt % dienes and 50 ppmv nitriles. 25 cc samples of each catalyst were used in a fixed bed reactor. The feedstock is hydrogenated at 120° C., 250 psi and LHSV=1 h−1. Conversion was evaluated after 6 hours on stream, and the results are set forth in Table 8 below.

TABLE 8

| Catalyst | Metal Ratio | Support | Dienes (%) | Nitrile (%) |
|---|---|---|---|---|
| Ni | — | zeolite-clay | 75 | 73 |
| Ni/Cu | 1:1 | zeolite-clay | 96 | 79 |
| Ni/Cu | 1:2 | zeolite-clay | 83 | 77 |
| Ni/Cu | 2:1 | zeolite-clay | 92 | 74 |
| Ni/Cu | 2:1 | zeolite-alumina | 100 | 95 |
| Ni/Cu | 7:1 | zeolite-alumina | 95 | 97 |
| Ni/Cu | 40:1 | zeolite-alumina | 91 | 89 |
| Ni/Co | 1:1 | zeolite-clay | 88 | 93 |
| Ni/Fe | 1:1 | zeolite-clay | 80 | 94 |

TABLE 8-continued

| Catalyst | Metal Ratio | Support | Dienes (%) | Nitrile (%) |
|---|---|---|---|---|
| Ni/Fe | 1:2 | zeolite-clay | 80 | 42 |
| Ni/Fe | 2:1 | zeolite-clay | 89 | 82 |

As shown, performance of the bimetallic catalyst of the present invention is superior to that of the monometallic catalyst.

EXAMPLE 8

This example shows the activity of completely reduced catalysts for treating the same feedstock under the same conditions as in Example 7. Catalysts were prepared using nickel, nickel/copper, nickel/cobalt and nickel iron, and each catalyst including the nickel/copper was completely reduced. Results are set forth in Table 9 below.

TABLE 9

| Catalyst | Metal Ratio | Support | Dienes (%) | Nitrile (%) |
|---|---|---|---|---|
| Ni | — | zeolite-clay | 100 | 97 |
| Ni/Cu | 2:1 | zeolite-clay | 77 | 79 |
| Ni/Co | 2:1 | zeolite-clay | 100 | 100 |
| Ni/Fe | 2:1 | zeolite-clay | 100 | 100 |

As shown, excellent results are obtained using completely reduced Group VIII metals. However, performance suffers when the Group VIII/Group IB bimetallic catalyst is completely reduced, including the Group IB metal.

EXAMPLE 9

This example illustrates the use of catalysts prepared as set forth in Example 7 in accordance with the invention for treating a feedstock having a nitrile content increased fourfold, treating under the same conditions as in Example 7. The results are set forth in Table 10 below.

TABLE 10

| Catalyst | Metal Ratio | Support | Dienes (%) | Nitrile (%) |
|---|---|---|---|---|
| Ni | — | zeolite-clay | 100 | 73 |
| Ni/Cu | 2:1 | zeolite-alumina | 100 | 100 |
| Ni/Co | 2:1 | zeolite-clay | 100 | 100 |

As shown, even at the increased levels of nitriles, excellent results are obtained using the bimetallic catalyst according to the invention.

EXAMPLE 10

This example shows the effect of the impregnation sequence on the performance of the catalyst for treating the feedstock of Example 7, using partially reduced catalysts. Catalysts were prepared using nickel and copper coimpregnated, nickel and then copper impregnated successively, and copper then nickel impregnated successively. The catalysts were calcined and then reduced after each impregnation step at the conditions appropriate to each type of metal. After final activation, the catalysts were used to treat the feedstock set forth above under the conditions of Example 7. The results are set forth below in Table 11.

TABLE 11

| Catalyst | Ni:Cu Ratio | Support | Dienes (%) | Nitrile (%) |
|---|---|---|---|---|
| Ni/Cu (coimp) | 2:1 | zeolite-clay | 100 | 97 |
| Ni/Cu | 2:1 | zeolite-clay | 100 | 100 |
| Cu/Ni | 2:1 | zeolite-clay | 77 | 79 |

As shown above, the order of impregnation as well as the presence of the second metal during calcination can modify the reducibility of the metals. As shown, impregnation with the Group VIII metal first provides for partially reduced Group IB and completely reduced Group VIII metals as desired, and better results are obtained with this catalyst (Ni/Cu).

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

We claim:

1. A catalyst useful for the simultaneous and selective hydrogenation of diolefins and nitriles present in a hydrocarbon feedstock, comprising:
    (a) a support material selected from the group consisting of inorganic oxide, carbon, zeolite and mixtures thereof; and
    (b) a catalytically active metal phase comprising at least two metals selected from the group consisting of partially reduced Group IB metals and completely reduced Group VIII metals, said active metal phase being present in an amount of out $\geq 0.03$ wt %.

2. A catalyst according to claim 1, wherein the support material is an inorganic oxide selected from the group consisting of silica, alumina, clay, titania, magnesia and mixtures thereof.

3. A catalyst according to claim 1 wherein the support material is an alumina-zeolite composite.

4. A catalyst according to claim 3 wherein the surface area of the catalyst is between about 100 to 1500 $m^2/g$.

5. A catalyst according to claim 3 wherein the surface area of the catalyst is between about 100 to 1000 $m^2/g$.

6. A catalyst according to claim 3 wherein the surface area of catalyst is between about 250 to 350 $m^2/g$.

7. A catalyst according to claim 3 wherein the pore volume of the catalyst is between about 0.20 cc/g to 1.50 cc/g.

8. A catalyst according to claim 3 wherein the pore volume of the catalyst is between about 0.30 cc/g to 0.70 cc/g.

9. A catalyst according to claim 1 wherein the active metal phase is present in an amount of between about 0.03 to 25 wt %.

10. A catalyst according to claim 1, wherein the Group VIII metal is selected from the group consisting of nickel, iron, cobalt, palladium and mixtures thereof, and the Group IB metal is copper.

11. A catalyst according to claim 1 wherein the active metal phase is nickel and copper.

12. A catalyst according to claim 1 wherein the active metal phase is nickel and cobalt.

13. A catalyst according to claim 1 wherein the active metal phase nickel and iron.

14. A method for preparing a catalyst useful for the simultaneous and selective hydrogenation of diolefins and nitriles present in a hydrocarbon feedstock, comprising the steps of:
(a) providing a support material selected from the group consisting of inorganic oxide, carbon, zeolite and mixtures thereof;
(b) impregnating the support material with a salt of a catalytically active metal phase comprising at least two metals selected from the group consisting of Group IB metals and Group VIII metals, said active metal phase being present in an amount of about $\geq 0.03$ wt % based on the final catalyst; and
(c) calcining and activating the impregnated support at a temperature between about 150° C. and about 650° C. so as to completely reduce said Group VIII metals and partially reduce said Group IB metals.

15. A method according to claim 14, wherein the impregnating step comprises impregnating the support material with metal salts of the at least two metals, and drying for a time sufficient to decompose the metal salts impregnated on the support.

16. A method according to claim 14, wherein the metal impregnating step comprises impregnating said support material with said Group VIII metal so as to provide a Group VIII metal impregnated support, calcining said Group VIII metal impregnated support so as to at least partially reduce said Group VIII metal, impregnating said Group VIII impregnated support with said Group IB metal so as to provide a final impregnated support, and calcining said final impregnated support, whereby said Group VIII metal is completely reduced and said Group IB metal is partially reduced.

17. A method according to claim 14 wherein the metal activating step comprises activating at a temperature of (°C.) 200–600, a pressure (psi) 15–350, and a $H_2$ flow rate (lt/h) of 0.1–8.0 so as to completely reduce said Group VIII metals.

18. A method according to claim 14 wherein the activating step comprises activating at a temperature of (°C.) 150–300, a pressure (psi) of 15–350, and a $H_2$ flow rate (lt/h) of 0.1–8.0 partially reduce said Group IB metals.

19. A method according to claim 17 wherein the activating step comprises activating at a temperature of (°C.) 150–300, a pressure (psi) of 15–350, and a $H_2$ flow rate (lt/h) of 0.1–8.0 so as to partially reduce said Group IB metal.

20. A method according to claim 14, wherein said support material is zeolite-alumina, and wherein said impregnating step comprises impregnating said support material with said Group IB metal so as to provide a Group IB metal impregnated support, calcining said Group IB metal impregnated support so as to partially reduce said Group IB metal, impregnating said Group IB metal impregnated support with said Group VIII metal so as to provide a final impregnated support, and calcining said final impregnated support so as to completely reduce said Group VIII metal, whereby said Group IB metal remains partially reduced.

21. A process for the simultaneous and selective hydrogenation of diolefins and nitriles from a hydrocarbon feedstock, comprising the steps of:
(a) providing a hydrocarbon feedstock having a diolefin content of $\geq 0.1$ wt % and a nitrile content of $\geq 2$ ppm(w);
(b) providing a catalyst comprising
 1) a support material selected from the group consisting of inorganic oxide, carbon, zeolite and mixtures thereof; and
 2) a catalytically active metal phase comprising at least two metals selected from the group consisting of partially reduced Group IB metals and completely reduced Group VIII metals, said active metal phase being present in an amount of about $\geq 0.03$ wt %.
(c) mixing the hydrocarbon feedstock in the presence of the catalyst with hydrogen wherein the ratio of hydrogen to the diolefins and nitriles in the feedstock is less than three times the stoichiometic amount required to selectively hydrogenate the diolefins and nitriles; and
(d) treating the feedstock and hydrogen mixture in the presence of the catalyst at a temperature of about between 50 to 250° C. at a pressure of between about 150 to 650 psi.

22. A process according to claim 21 wherein said temperature is between about 60 to 160° C.

23. A process according to claim 21 wherein the pressure is between 200 to 400 psi.

24. A process according to claim 21 wherein the liquid hourly space velocity is in the range of between about 0.1 to 5 $h^{-1}$.

25. A process according to claim 21 wherein the liquid hourly space velocity is in the range of between about 0.5 to 5 $h^{-1}$.

26. A process according to claim 21 wherein the liquid hourly space velocity is in the range of between about 1 to 4.5 $h^{-1}$.

* * * * *

UNITED STATES PATENT AND TRADEMARK OFFICE
CERTIFICATE OF CORRECTION

PATENT NO. : 5,948,942
DATED : September 7, 1999
INVENTOR(S) : MAGDALENA RAMIREZ DE AGUDELO ET AL.

It is certified that error appears in the above-identified patent and that said Letters Patent is hereby corrected as shown below:

In Column 2, line 41, "nitrites" should read --nitriles--;

In Column 2, line 53, "nitrites" should read --nitriles--;

In Column 5, line 3, "h-1" should read --$h^{-1}$--;

In Column 6, line 4, "3h-1" should read --$3h^{-1}$--;

In Column 6, line 26, "nitrites" should read --nitriles--;

In Column 6, line 30, "specifically" should read --Specifically--;

In Column 6, line 66, "nitrites" should read --nitriles--;

In Column 8, line 53, "h-1" should read --$h^{-1}$--;

In Column 10, claim 6, line 48, before "catalyst" the word --the-- should be inserted;

UNITED STATES PATENT AND TRADEMARK OFFICE
CERTIFICATE OF CORRECTION

PATENT NO. : 5,948,942
DATED : September 7, 1999
INVENTOR(S) : MAGDALENA RAMIREZ DE AGUDELO ET AL.

It is certified that error appears in the above-identified patent and that said Letters Patent is hereby corrected as shown below:

In Column 10, claim 13, line 67, after "phase"
the word --is-- should be inserted; and In Column 11, claim 18, line 43, after "0.1-8.0"
--so as to-- should be inserted.

Signed and Sealed this

Eighteenth Day of April, 2000

Q. TODD DICKINSON

Attest:

Attesting Officer

Director of Patents and Trademarks